United States Patent
Shirota et al.

(10) Patent No.: US 10,646,103 B2
(45) Date of Patent: May 12, 2020

(54) DRIVE DEVICE

(71) Applicant: OLYMPUS CORPORATION, Tokyo (JP)

(72) Inventors: Yutaka Shirota, Hino (JP); Masaaki Watanabe, Hachioji (JP); Takahiro Hayama, Hino (JP); Ayuko Kumada, Sukagawa (JP)

(73) Assignee: OLYMPUS CORPORATION, Tokyo (JP)

( * ) Notice: Subject to any disclaimer, the term of this patent is extended or adjusted under 35 U.S.C. 154(b) by 323 days.

(21) Appl. No.: 15/692,457

(22) Filed: Aug. 31, 2017

(65) Prior Publication Data
US 2017/0360276 A1 Dec. 21, 2017

Related U.S. Application Data

(63) Continuation of application No. PCT/JP2016/066373, filed on Jun. 2, 2016.

(30) Foreign Application Priority Data

Jul. 2, 2015 (JP) .................................. 2015-133679

(51) Int. Cl.
A61B 1/00 (2006.01)
A61B 1/06 (2006.01)
(Continued)

(52) U.S. Cl.
CPC ............ *A61B 1/00013* (2013.01); *A61B 1/00* (2013.01); *A61B 1/00048* (2013.01);
(Continued)

(58) Field of Classification Search
CPC ........... A61B 1/045; A61B 1/043; A61B 1/06; A61B 1/0638; A61B 1/0646; A61B 1/0653; A61B 1/0661
(Continued)

(56) References Cited

U.S. PATENT DOCUMENTS 4,396,288 A * 8/1983 Helphrey .................. G01J 3/12
356/326
4,862,253 A * 8/1989 English ................ H04N 5/2254
348/269

(Continued)

FOREIGN PATENT DOCUMENTS

JP H11-326785 A 11/1999
JP 2009-226072 A 10/2009
(Continued)

OTHER PUBLICATIONS

International Search Report dated Aug. 23, 2016 issued in PCT/JP2016/066373.

Primary Examiner — Matthew J Kasztejna
(74) Attorney, Agent, or Firm — Scully, Scott, Murphy & Presser, P.C.

(57) ABSTRACT

A drive device includes a filter section that includes an optical filter, a transmission section that rotates around a rotation shaft, a first groove portion that is formed to the transmission section, a protruding portion that is formed to the filter section, in contact with the first groove portion, and that moves the filter section from a first position to a second position by moving along the first groove portion in coordination with rotation of the transmission section, and a second groove portion that is formed continuously with the first groove portion, and that is provided along a tangent line direction passing through the protruding portion that is on a circle having the rotation shaft of the transmission section at a center and a radius that is a distance between the rotation shaft and the protruding portion, when the optical filter section is moved to the second position.

5 Claims, 5 Drawing Sheets

(51) Int. Cl.
   *A61B 1/04*   (2006.01)
   *A61B 1/045*  (2006.01)
   *A61B 1/05*   (2006.01)
   *G02B 23/26*  (2006.01)

(52) U.S. Cl.
   CPC .............. *A61B 1/043* (2013.01); *A61B 1/045* (2013.01); *A61B 1/053* (2013.01); *A61B 1/06* (2013.01); *A61B 1/0005* (2013.01); *A61B 1/00188* (2013.01); *A61B 1/0638* (2013.01); *G02B 23/26* (2013.01)

(58) Field of Classification Search
   USPC .................................................. 600/178–182
   See application file for complete search history.

(56) References Cited

U.S. PATENT DOCUMENTS

| | | | | |
|---|---|---|---|---|
| 4,885,635 | A * | 12/1989 | Kimura | A61B 1/00105 348/70 |
| 6,817,788 | B1 * | 11/2004 | Negishi | G03B 11/00 348/342 |
| 7,158,323 | B2 * | 1/2007 | Kim | G02B 26/007 348/235 |
| 2004/0258405 | A1 * | 12/2004 | Shiratori | G03B 9/14 396/458 |
| 2013/0148345 | A1 * | 6/2013 | Yabe | A61B 1/0638 362/231 |

FOREIGN PATENT DOCUMENTS

| | | |
|---|---|---|
| JP | 2012-010981 A | 1/2012 |
| WO | WO 2011/125457 A1 | 10/2011 |

\* cited by examiner

DRIVE DEVICE

CROSS REFERENCE TO RELATED APPLICATION

This application is a continuation application of PCT/JP2016/066373 filed on Jun. 2, 2016 and claims benefit of Japanese Application No. 2015-133679 filed in Japan on Jul. 2, 2015, the entire contents of which are incorporated herein by this reference.

BACKGROUND OF THE INVENTION

1. Field of the Invention

The present invention relates to a drive device for an observation light switching mechanism which is configured to perform switching of observation light by inserting or removing an optical filter on an optical path of a light source device for an endoscope.

2. Description of the Related Art

Conventionally, endoscopes including an elongated tubular insertion section have been widely used in medical and industrial fields, for example. Among such endoscopes, a medical endoscope used in the medical field is configured to be able to observe an organ or the like by having the insertion section inserted into a body cavity of a subject, such as a living body, and to perform various treatments on the organ or the like as necessary by using a treatment instrument that is inserted in a treatment instrument insertion channel provided to the endoscope. Also, an industrial endoscope used in the industrial field is configured to be able to observe or inspect the state, such as a scratch or corrosion, inside an object, by having the insertion section inserted into an object such as a device or equipment such as a jet engine or a pipe in a factory.

An observation target of such an endoscope is usually a subject or an object in a dark place, such as inside a body cavity or inside a device, and a light source device for illuminating such a subject or an object becomes necessary.

Some conventional light source devices for an endoscope are configured to allow setting of a plurality of observation modes, such as special-light observation such as narrow band imaging (NBI), in addition to normal light (white light) observation, and a user is to set an appropriate observation mode according to an observation target.

According to a configuration of a conventional light source device for an endoscope capable of handling a plurality of observation modes, light according to a plurality of observation modes may be emitted by inserting or removing an optical filter for wavelength conversion, light reduction or the like on an optical path of an emitting light source to which a xenon lamp, an LED (light emitting diode), an LD (laser diode) or the like which is internally provided is applied. Accordingly, this type of light source device for an endoscope is provided with an observation light switching mechanism which is configured to perform switching of illumination light for observation by inserting or removing an optical filter on an optical path of an emitting light source.

As an observation light switching mechanism of a conventional light source device for an endoscope, various modes are proposed by International Publication No. WO2011/125457 and the like, and are being put to practical use.

The light source device for an endoscope disclosed in International Publication No. WO2011/125457 described above includes an observation light switching mechanism which is configured to perform switching of emitted light by attaching a disk retaining an optical filter (hereinafter referred to as a filter retaining plate) to a rotation shaft of a drive motor, rotating the filter retaining plate by a rotational drive force of the drive motor, and thereby arranging the optical filter of the filter retaining plate on the optical path of the emitting light source.

SUMMARY OF THE INVENTION

A drive device according to an aspect of the present invention includes a filter section that includes an optical filter, a transmission section that rotates around a predetermined rotation shaft, a first groove portion that is formed to the transmission section, a protruding portion that is formed to the filter section, in contact with the first groove portion, and that moves the filter section from a first position to a second position different from the first position by moving along the first groove portion in coordination with rotation of the transmission section, and a second groove portion that is formed continuously with the first groove portion, and that is provided along a tangent line direction passing through the protruding portion that is on a circle having the rotation shaft of the transmission section at a center and a radius that is a distance between the rotation shaft and the protruding portion, in a state where the filter section is moved to the second position.

DETAILED DESCRIPTION OF THE PREFERRED EMBODIMENT(S)

Figure 1:
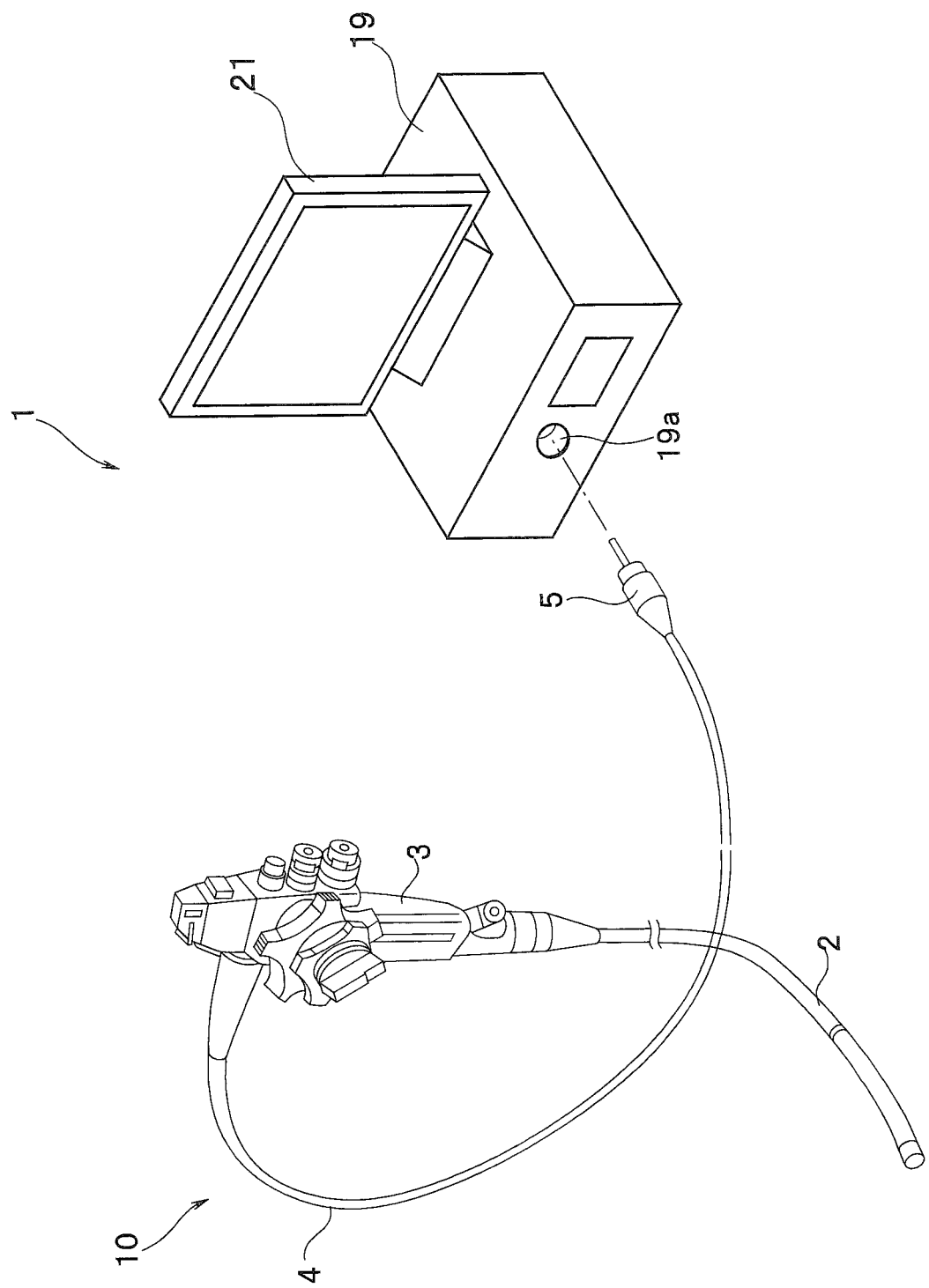
FIG. 1 is a schematic perspective view showing an overall configuration of an endoscope system including a light source device, for an endoscope, provided with a drive device of an embodiment of the present invention.

Hereinafter, the present invention will be described using an embodiment illustrated in the drawings. Each of the drawings used in the following description is schematic, and the dimensional relationship, the scale and the like of each member may be shown differently for each structural component such that each structural component is shown to be large enough to be recognized in the drawing. Accordingly, the present invention is not limited to the modes shown in the drawings with respect to the number of structural components, the shapes of the structural components, the proportion of the sizes of the structural components, and the relative positional relationship of respective structural components.

Figure 2:
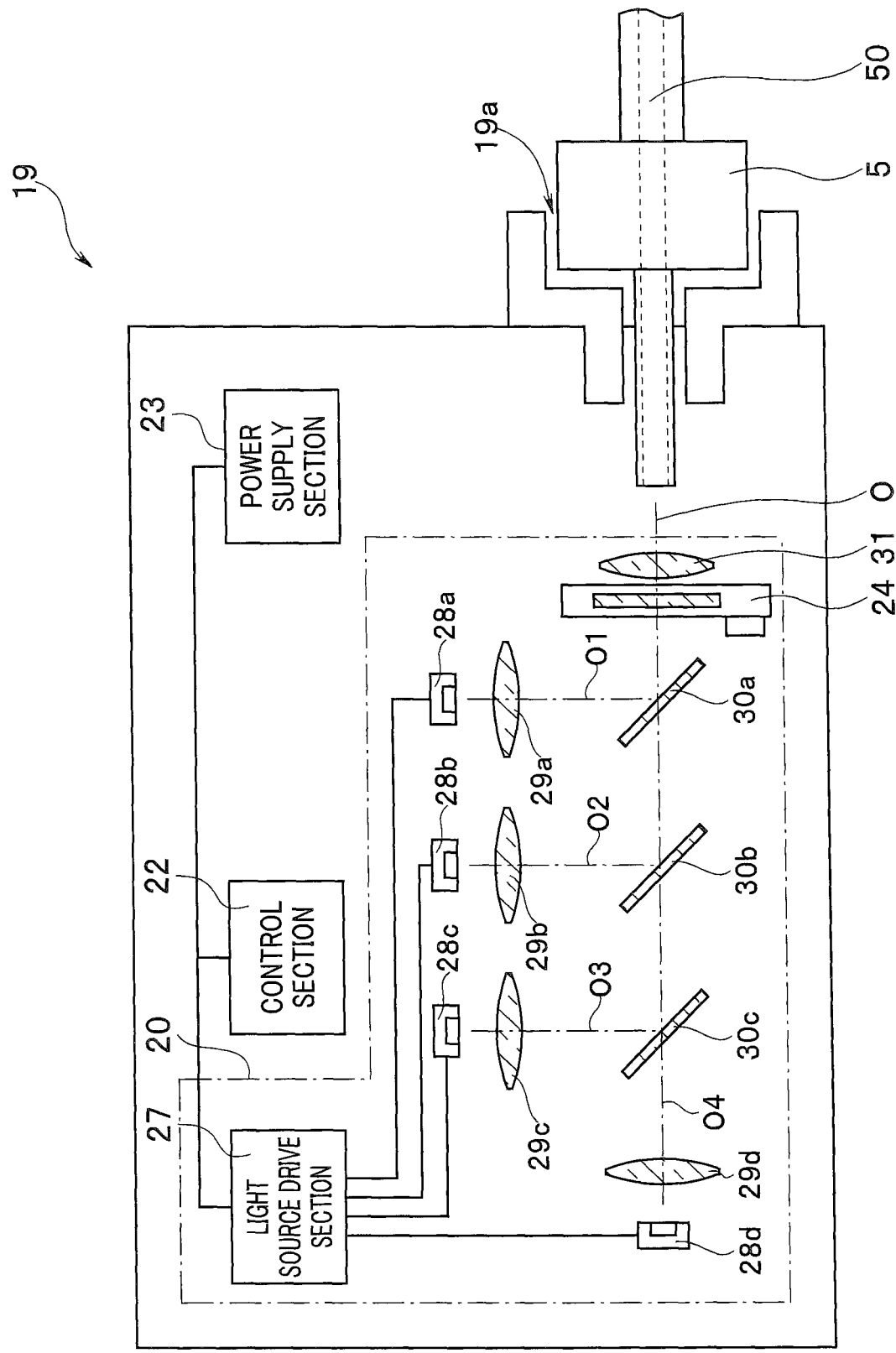
FIG. 2 is a schematic block diagram showing main components inside the light source device, for an endoscope, in the endoscope system in FIG. 1.
Figure 3:
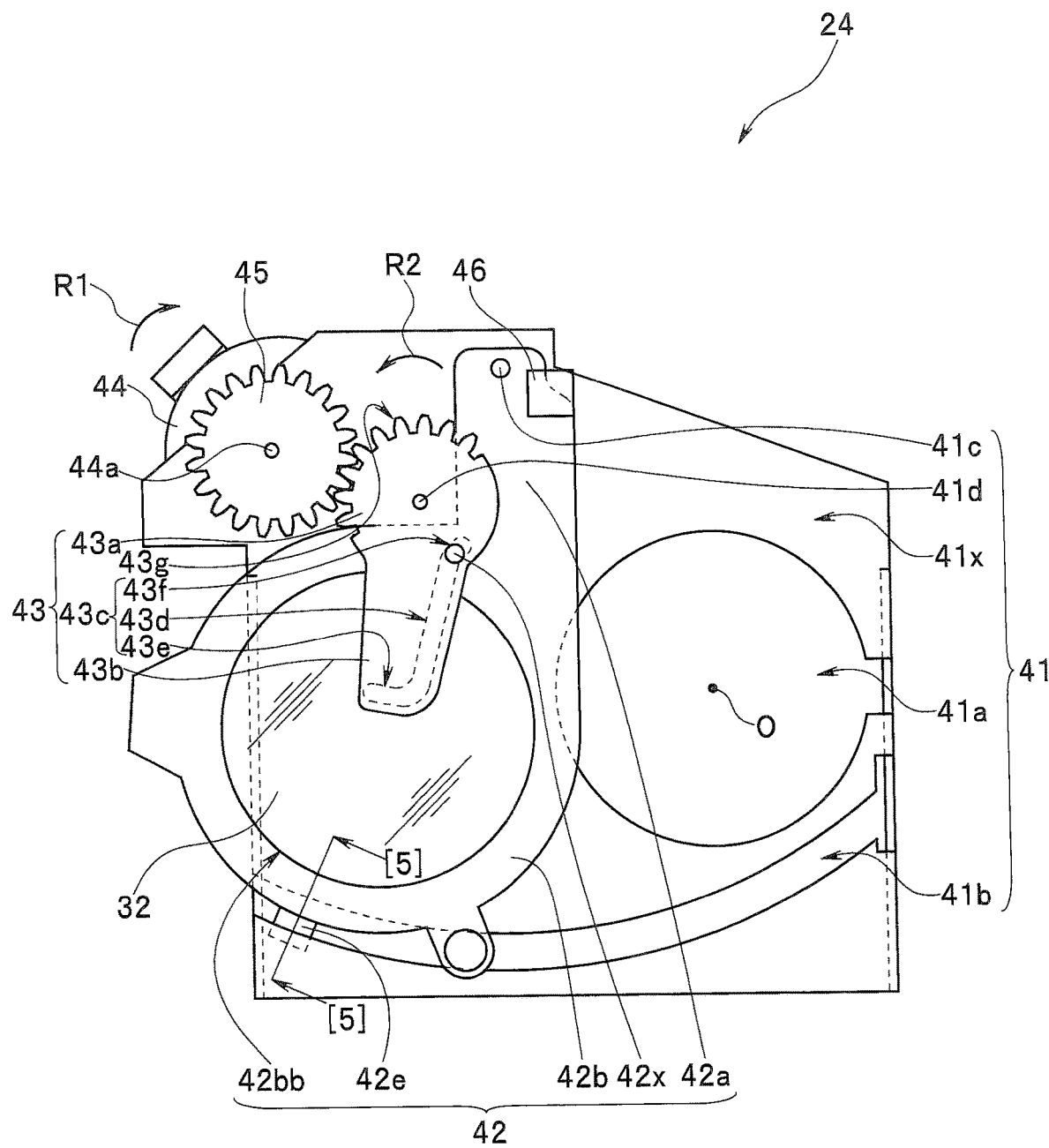
FIG. 3 is a plan view showing a configuration of the drive device according to the present embodiment (showing a state where an optical filter is at a first position)
Figure 4:
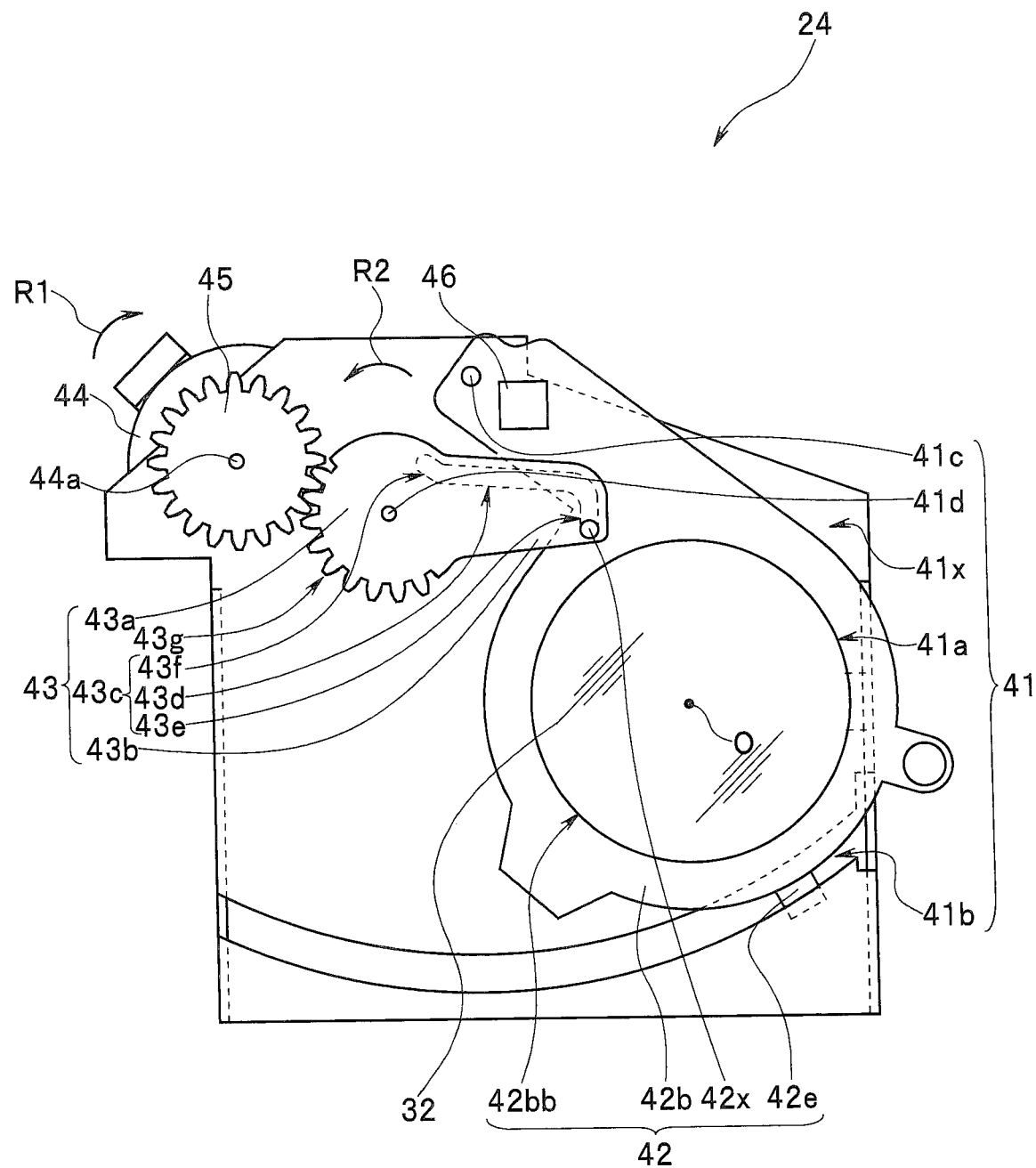
FIG. 4 is a plan view describing an action of the drive device in FIG. 3 (showing a state where the optical filter is at a second position)
Figure 5:
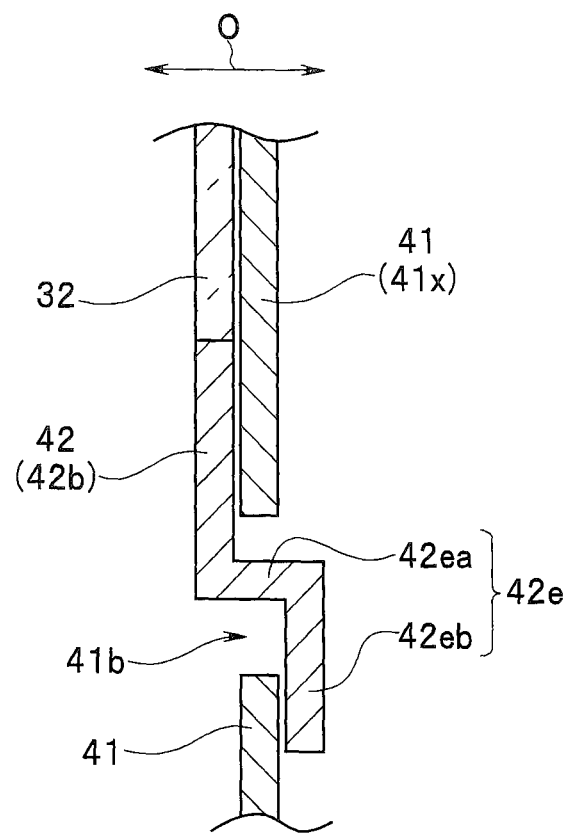
FIG. 5 is an enlarged cross-sectional view showing main parts along line [5]-[5] in FIG. 3.

FIGS. 1 to 5 are diagrams showing an embodiment of the present invention. Among the diagrams, FIG. 1 is a schematic perspective view showing an overall configuration of an endoscope system including a light source device, for an endoscope, provided with a drive device of the present embodiment. FIG. 2 is a schematic block diagram showing main components inside the light source device, for an endoscope, in the endoscope system in FIG. 1. FIG. 3 is a plan view showing a configuration of the drive device, according to the present embodiment, included in the light source device for an endoscope in FIG. 2. FIG. 4 is a view describing an action of the drive device in FIG. 3. Note that FIG. 3 shows a state where an optical filter of the drive device is at a first position. FIG. 4 shows a state where the optical filter of the drive device in FIG. 3 is at a second position. FIG. 5 is an enlarged cross-sectional view showing main parts along line [5]-[5] in FIG. 3.

First, before giving details about a drive device of the present embodiment (see FIGS. 2 to 4), a configuration of an endoscope system 1 including a light source device, for an endoscope, provided with the drive device will be briefly described below with reference mainly to FIGS. 1 and 2.

As shown in FIG. 1, the endoscope system 1 is configured mainly from an endoscope 10, a control unit 19, a display device 21, and the like. For example, the endoscope system 1 is a system which is configured to convert an optical image of a desired observation part inside a subject or an object, such as a human body or a building, into an image signal by the endoscope 10, to subject the acquired image signal to various types of signal processing by a control section 22 of the control unit 19, and to output the signal after processing to the display device 21 so as to be displayed as an image or to output the signal after processing to a recording device, not shown, so as to be stored.

The endoscope 10 is configured with an insertion section 2, an operation section 3, a universal cable 4, a connector section 5, and the like.

The entire insertion section 2 is elongated and flexible. A predetermined range on a distal end side of the insertion section 2 is a bending portion, which is formed to be bendable. An image pickup section, an illumination section and the like are provided inside a most distal end portion of the insertion section 2. The image pickup section here is formed of a CCD image pickup device or a CMOS image pickup device. Also, the image pickup section may be an image pickup device having a complementary color filter at the front. Alternatively, the image pickup section may be configured with three image pickup devices corresponding respectively to R, G and B obtained by branching RGB light by a dichroic mirror. Moreover, the image pickup section may be configured with a double-plate image pickup device capable of handling green light separated by a dichroic mirror and light of other colors. Note that internal components, such as various signal lines, a light guide, an air/water feeding pipe and a treatment instrument insertion channel, are inserted and arranged inside the insertion section 2, from a distal end to a proximal end.

The operation section 3 is provided continuously with the proximal end of the insertion section 2, and various operation members and the like are provided on an outer surface. Various signal lines, the light guide, the air/water feeding pipe and the like extending from the insertion section 2 are inserted and arranged inside the operation section 3, and also, an electric board or the like on which an electronic circuit or the like for receiving input signals from the operation members is installed in the operation section 3.

The universal cable 4 extends from the operation section 3, and various signal lines, the light guide, the air/water feeding pipe and the like are inserted and arranged inside the universal cable 4.

The connector section 5 is provided continuously with a distal end of the universal cable 4, and is shaped as a plug so as to be attachable/detachable to/from a connection section 19a of the control unit 19.

The endoscope 10 itself is the same as a conventional endoscope which is generally and widely used, and thus, detailed description of other components is omitted.

As shown in FIG. 2, the control unit 19 includes a light source device 20 for an endoscope, a control section 22, a power supply section 23, and the like. Note that the control unit 19 also includes other components, but those components are not directly relevant to the present invention, and illustration and description thereof are omitted.

The control section 22 is a structural unit configured to control the operation of the entire endoscope system 1 in an overall manner based on predetermined programs and the like, and also, to be able to perform various types of signal processing by receiving image pickup signals acquired and outputted by the endoscope 10. Accordingly, the control section 22 performs display control of outputting an image signal for display, generated as a result of signal processing, to the display device 21 and of causing an image to be displayed on a display screen of the display device 21, and storage control of outputting image data for recording, generated as a result of signal processing, to a storage device (not shown) and of causing the image data to be stored in the storage device, for example. Therefore, the control section 22 is configured by including an arithmetic control/signal processing device (CPU), a storage device (RAM), an auxiliary storage device, an input/output device, and the like.

The power supply section 23 is a structural unit configured to supply power for driving each part constituting the endoscope system 1.

As shown in FIGS. 1 and 2, the control unit 19 includes the connection section 19a, which is formed to allow attachment/detachment of the connector section 5 of the endoscope 10. The connection section 19a is provided to a front panel of a housing of the control unit 19 (see FIG. 1), for example.

A proximal end of an optical fiber cable 50, which is inserted into the insertion section 2 of the endoscope 10 from the universal cable 4 via the operation section 3, is installed at the connector section 5. In a state where the connector section 5 is fitted and connected to the connection section 19a, the proximal end of the optical fiber cable 50 is arranged at an incident position of light that is emitted from the light source device 20 for an endoscope (described in detail below). Light entering the proximal end of the optical fiber cable 50 is thereby guided to a distal end portion of the insertion section 2 of the endoscope 10 by the optical fiber cable 50 and is emitted outside from an illumination window (not shown) to illuminate a subject.

The light source device 20 for an endoscope is a structural unit which is configured to generate light for illuminating a target object which is to be observed using the endoscope 10. The light source device 20 for an endoscope mainly includes a light source drive section 27, a plurality of light source elements 28(a to d), a plurality of collimator lenses 29(a to d), a plurality of dichroic mirrors 30(a to c), a condenser lens 31, an observation light switching mechanism unit 24, and the like.

The light source drive section 27 is a structural section including a drive circuit for driving the plurality of light source elements 28(*a* to *d*) according to an instruction signal from the control section 22, for example.

The plurality of light source elements 28(*a* to *d*) are light emitters to which solid-state light-emitting devices, such as laser diodes or light-emitting diodes (LED), are applied. The light source device 20 for an endoscope includes a function of causing emitted light from the plurality of light source elements 28(*a* to *d*) to enter the proximal end of the optical fiber cable 50 of the connector section 5.

The present embodiment illustrates an example where four light source elements 28(*a* to *d*) are provided. The plurality of light source elements 28(*a* to *d*) are LEDs that emit light in predetermined respective wavelength ranges having different wavelengths at the center. More specifically, the plurality of light source elements 28(*a* to *d*) are a red LED 28*a*, a green LED 28*b*, a blue LED 28*c*, and a purple LED 28*d*, for example. Note that the wavelength of emitted light of each light source element 28(*a* to *d*) is not particularly specified. Moreover, the number of the plurality of light source elements 28 provided to the light source device 20 for an endoscope is not limited to four, as illustrated in the form of the present embodiment, as long as the number is two or more.

Moreover, instead of an LED, a fluorescent light source may be used which radiates excitation light on phosphor that generates blue light, green light or red light, and which emits excitation light which has passed through the phosphor and fluorescent light from the phosphor.

The plurality of light source elements 28(*a* to *d*) are each electrically connected to the light source drive section 27, and are each configured to emit light as appropriate according to an instruction signal outputted from the light source drive section 27. Moreover, intensity of light that is emitted from each of the plurality of light source elements 28(*a* to *d*) is changed according to an instruction signal outputted from the light source drive section 27.

The plurality of collimator lenses 29(*a* to *d*) are provided corresponding to the plurality of light source elements 28(*a* to *d*), and include a function of transmitting emitted light from the respective light source elements 28(*a* to *d*) and of emitting the light as parallel light.

The plurality of dichroic mirrors 30(*a* to *c*) include a function of receiving the parallel light emitted from the plurality of collimator lenses 29(*a* to *d*) and of guiding the light to the condenser lens 31. The present embodiment illustrates an example where three dichroic mirrors 30(*a* to *c*) are provided. In the case of using fluorescent light sources as the light source elements, excitation light is desirably removed from illumination light by the plurality of dichroic mirrors 30(*a* to *c*).

The condenser lens 31 includes a function of transmitting emitted light from the plurality of light source elements 28(*a* to *d*) guided by the plurality of dichroic mirrors 30(*a* to *c*), and of condensing the emitted light toward the proximal end of the optical fiber cable 50 of the connector section 5.

The observation light switching mechanism unit 24 is installed between the plurality of dichroic mirrors 30(*a* to *c*) and the condenser lens 31, and includes a function of performing switching of observation light by inserting or removing an optical filter 32 (described in detail below) on an optical path of a light flux which is guided to the condenser lens 31 by the plurality of dichroic mirrors 30(*a* to *c*).

A specific example of arrangement of the plurality of light source elements 28 (*a* to *d*), the plurality of collimator lenses 29(*a* to *d*), the plurality of dichroic mirrors 30(*a* to *c*), the condenser lens 31 and the like of the light source device 20 for an endoscope will be described with reference to FIG. 2.

Note that an axis passing through the center axis of the condenser lens 31 is taken as an optical axis O. The optical axis O is a center axis of emitted light from the light source device 20 for an endoscope. Moreover, the optical paths of respective emitted light from the plurality of light source elements 28(*a* to *d*) are denoted by reference signs O1, O2, O3 and O4. Here, the optical path O4 of the purple LED 28*d* is parallel to the optical path O. Moreover, the three collimator lenses 29*a*, 29*b*, 29*c* are installed with respective optical axes coinciding with the corresponding optical paths O1, O2, O3.

As shown in FIG. 2, in the present case, the purple LED 28*d*, among the plurality of light source elements 28(*a* to *d*), is installed on the optical axis O. On the other hand, other three light source elements 28, among the plurality of light source elements 28(*a* to *d*), that is, the red LED 28*a*, the green LED 28*b*, and the blue LED 28*c* are installed at positions offset from the optical axis O. The red LED 28*a*, the green LED 28*b*, and the blue LED 28*c* are installed with the respective optical paths O1, O2, O3 being orthogonal to the optical axis O (optical path O4). Note that the three light source elements (28*a*, 28*b*, 28*c*) are installed on one side of the optical axis O (optical path O4).

Moreover, the three dichroic mirrors 30(*a* to *c*) are disposed along the optical axis O, in the order of 30*a*, 30*b*, 30*c* from the side of the condenser lens 31. At the same time, the three dichroic mirrors 30*a*, 30*b*, 30*c* are installed on the extension of the respective optical paths O1, O2, O3. According to such a configuration, each of reflection surfaces of the three dichroic mirrors 30*a*, 30*b*, 30*c* is installed at an angle of 45 degrees to the optical axis O, at a position where the optical axis O (optical path O4) and each of the optical paths O1, O2, O3 intersect with each other at a substantially right angle.

Note that the reflection surface of the dichroic mirror 30*a* reflects light in a predetermined wavelength range including the wavelength of emitted light from the red LED 28*a*, and transmits light in other wavelength ranges. Also, the reflection surface of the dichroic mirror 30*b* reflects light in a predetermined wavelength range including the wavelength of emitted light from the green LED 28*b*, and transmits light in other wavelength ranges. Moreover, the reflection surface of the dichroic mirror 30*c* reflects light in a predetermined wavelength range including the wavelength of emitted light from the blue LED 28*c*, and transmits light in other wavelength ranges.

According to such a configuration, emitted light from the purple LED 28*d* is transmitted through the collimator lens 29*d* to be made parallel light, and is then transmitted through the dichroic mirrors 30*a*, 30*b*, 30*c* to enter the condenser lens 31 via the observation light switching mechanism unit 24. On the other hand, emitted light from each of the red LED 28*a*, the green LED 28*b*, and the blue LED 28*c* is transmitted through the collimator lens 29*a*, 29*b*, 29*c* to be made parallel light, is reflected by the dichroic mirror 30*a*, 30*b*, 30*c*, and is then combined with the emitted light from the collimator lens 29*d* to enter the condenser lens 31 via the observation light switching mechanism unit 24.

According to such a configuration, the light source device 20 for an endoscope is enabled to emit various types of observation light by combining four light source elements 28(*a* to *d*) and causing the light source elements to emit light.

For example, in the case of a normal light observation operation mode (white light observation mode) of emitting white light for normal observation as observation light, the red LED 28a, the green LED 28b, and the blue LED 28c are caused to emit light at the same time. Also, in the case of special-light observation operation mode of emitting special light as observation light, as in the case of narrow band imaging, the green LED 28b and the purple LED 28d are caused to emit light at the same time.

Furthermore, in the normal light observation operation mode, the control section 22 drives the light source drive section 27, while taking into account a spectral sensitivity of the image pickup section in the endoscope 10, in such a way that an amounts of light of the LEDs are made green >blue >red. Moreover, to enhance the color reproducibility for an object, the control section 22 may illuminate the purple LED 28d. Also in the narrow band imaging mode, the light source drive section 27 is driven, while taking into account attenuation of light of short wavelength from the purple LED 28d, in such a way that a ratio of the amounts of light of the LEDs are made purple >green.

In addition to the normal light observation operation mode and the narrow band imaging mode, switching to a naked eye observation mode in which a subject is observed with naked eyes may also be allowed. In the case of switching to the naked eye observation mode, the control section 22 makes the amount of red light greater than the amount of blue light, compared with the normal light observation operation mode, and drives the light source drive section 27 in such a way that the amounts of light of the LEDs are made green >red >blue.

Moreover, the color tone of an observation image changes depending on the property of the light guide in a scope or the spectral sensitivity of the image pickup device, and thus, the ratio of the amounts of light is not limited to the ratios described above.

In the case where the purple LED 28d is not caused to emit light in the normal light observation operation mode, a drive circuit may be shared between the purple LED 28d and another LED (such as the blue LED 28c). In such a case, a common drive circuit is connected to an anode side of the purple LED 28d and an anode side of the blue LED 28c, and the cathode sides of the LEDs are connected to the ground via switches a and b. In the normal light observation operation mode, control is performed such that a drive control signal for controlling the amount of light emission of the blue LED 28c used for normal observation is outputted to the drive circuit, and a switch a for the purple LED 28d is turned off and a switch b for the blue LED 28c is turned on. In the narrow band imaging mode, control is performed such that a drive control signal for controlling the amount of light emission of the purple LED 28d used for observation is outputted to the drive circuit, and the switch a for the purple LED 28d is turned on and the switch b for the blue LED 28c is turned off.

In addition, in the present embodiment, the observation light switching mechanism unit 24 is provided. For example, the observation light switching mechanism unit 24 is a mechanism unit configured to perform switching of the observation light by inserting or removing the optical filter 32 for generating light of a predetermined wavelength characteristic on the optical axis O (optical path O4). For example, the optical filter 32 is an ND (neutral density) filter for wavelength conversion or for light reduction, or a narrow band filter, used in the narrow band imaging mode, which is configured to transmit light from the purple LED 28d and to transmit only the light in the narrow band in the green light emitted by the green LED 28b so as to increase the visibility of a blood vessel. For example, even if the transmissivity of the narrow band filter is made the same for the purple light and the green light, a desirable light emission ratio may be maintained with respect to the amounts of purple light and green light in the narrow band, which are radiated in the narrow band imaging mode, because the amounts of light may be independently controlled by the control of the green LED 28b and the purple LED 28d.

A configuration of the observation light switching mechanism unit 24 will be described in detail below with reference to FIGS. 3, 4 and 5.

As described above, the observation light switching mechanism unit 24 is disposed, in the light source device 20 for an endoscope, between the plurality of dichroic mirrors 30(a to c) and the condenser lens 31. That is, the observation light switching mechanism unit 24 is arranged just before a position where the emitted light from the plurality of light source elements 28(a to d) is finally guided to the condenser lens 31.

As shown in FIG. 3 and the like, the observation light switching mechanism unit 24 is configured mainly from a base 41, which is a base member, a filter retaining plate 42, which is a filter section, a cam 43, which is a transmission section, a drive motor 44, which is a drive source, a drive gear 45, which is a drive section, a photointerrupter 46, which is a position detection section, and the like.

The base 41, which is a base member, is a basic structural body of the observation light switching mechanism unit 24. The base 41 is a structural component that is formed by subjecting a flat metal plate member to sheet metal processing such as cutting and bending, for example. The base 41 is fixed at a predetermined position inside the observation light switching mechanism unit 24 (i.e., between the dichroic mirror 30a and the condenser lens 31), with a main flat surface 41x of the base 41 being a surface that is orthogonal to the optical axis O (optical path O4). A through hole 41a is drilled into the main flat surface 41x of the base 41. The through hole 41a is formed at a position at which the center axis substantially coincides with the optical axis O (optical path O4). With such a configuration, emitted light from the light source elements 28(a to d) propagating along the optical axis O (optical path O4) passes through the through hole 41a.

Moreover, a filter retaining plate guide groove 41b is formed at a position near an edge portion on one side of the base 41 (in the present embodiment, near the lower portion shown in FIG. 3). The filter retaining plate guide groove 41b is a structural component including functions of guiding rotation of the filter retaining plate 42, and of suppressing tilting of the filter retaining plate 42 in the direction of the optical axis O (that is, in the direction orthogonal to the flat surface of the main flat surface 41x of the base 41). Therefore, a tilt suppressing portion 42e of the filter retaining plate 42 slidably engages with the filter retaining plate guide groove 41b, as described below. Note that details of engagement of the filter retaining plate guide groove 41b and the tilt suppressing portion 42e of the filter retaining plate 42 will be given below.

The filter retaining plate 42, the cam 43, and the drive motor 44 are installed at predetermined positions of the base 41. For example, among the components, the drive motor 44 is fixed near one corner portion on an upper end side of the base 41, with a drive shaft 44a, which is a rotation shaft of the drive motor 44, being parallel to the optical axis O. Also, for example, the filter retaining plate 42 is installed near an edge portion on one side on the upper end side of the base 41, in a manner capable of rotating on a plane parallel to the main flat surface 41x with a support shaft 41c protruding in parallel to the optical axis O as a rotation axis (rotation center). Moreover, for example, the cam 43 is installed near the drive motor 44, in a manner capable of rotating on the plane parallel to the main flat surface 41x with a support shaft 41d protruding in parallel to the optical axis O as a rotation axis (rotation center).

The filter retaining plate 42, which is a filter section, is a structural member for retaining the optical filter 32 while allowing the optical filter 32 to be arranged at a first position (position shown in FIG. 3) and a second position (position shown in FIG. 4) different from the first position.

Note that the first position of the optical filter 32 is a position of the optical filter 32 which is retracted from the through hole 41a, that is, the position shown in FIG. 3. Also, the second position is a position of the optical filter 32 covering the through hole 41a, that is, the position shown in FIG. 4. In other words, the second position is a position of the optical filter 32 which is on the optical axis O and which is inserted in the optical path O4.

For example, the filter retaining plate 42 is a structural component which is formed by subjecting a flat metal plate member to sheet metal processing such as cutting and bending. The filter retaining plate 42 is pivotally supported to the base 41 by the support shaft 41c in a manner capable of rotating on the plane parallel to the main flat surface 41x of the base 41.

The filter retaining plate 42 is formed to include a support arm portion 42a, a filter retaining portion 42b, the tilt suppressing portion 42e, a cam pin 42x, which is a protruding portion, and the like.

The support arm portion 42a of the filter retaining plate 42 is pivotally and rotatably supported to the support shaft 41c, which is provided to the main flat surface 41x of the base 41 in a standing manner. The filter retaining portion 42b for fixedly installing the optical filter 32 is formed at a distal end side of the support arm portion 42a of the filter retaining plate 42. A through window portion 42bb having a diameter slightly smaller than that of the optical filter 32 is drilled into the filter retaining portion 42b. The optical filter 32 is installed in a manner covering the through window portion 42bb. With such a configuration, the through window portion 42bb drilled into the filter retaining portion 42b is configured to allow passing of a light flux which is transmitted through the optical filter 32, which is fixedly installed to the filter retaining portion 42b.

Moreover, the tilt suppressing portion 42e is formed at a side edge portion near a distal end of the filter retaining portion 42b. As shown in FIG. 5, the tilt suppressing portion 42e is configured with a bent arm portion 42ea extending along the optical axis O, from the side edge portion of the filter retaining portion 42b of the filter retaining plate 42 to a back surface side of the base 41 through the filter retaining plate guide groove 41b, and a suppressing arm portion 42eb extending, along a back surface of the main flat surface 41x, from an outer circumferential distal end portion of the bent arm portion 42ea in a direction parallel to the main flat surface 41x of the base 41 (i.e., direction orthogonal to the optical axis O).

With such a configuration, when the filter retaining plate 42 is rotated with the support shaft 41c as the rotation axis (rotation center), the tilt suppressing portion 42e moves along the filter retaining plate guide groove 41b. At this time, the tilt suppressing portion 42e suppresses tilting of the filter retaining plate 42. Interference with other structural members installed near the filter retaining plate 42 may thereby be prevented, for example.

Note that, when the optical filter 32 retained by the filter retaining plate 42 is at the first position shown in FIG. 3, for example, the optical filter 32 is at a position at which the optical filter 32 is retracted from the through hole 41a of the main flat surface 41x of the base 41. On the other hand, when the optical filter 32 is at the second position shown in FIG. 4, for example, the optical filter 32 is at a position at which the optical filter 32 covers the through hole 41a of the main flat surface 41x of the base 41 (i.e., position at which the optical filter 32 is on the optical axis O and is inserted in the optical path O4). Accordingly, at this time, a light flux passing through the through hole 41a and traveling toward the condenser lens 31 is converted by the optical filter 32 into light of a predetermined wavelength characteristic.

Accordingly, when the filter retaining plate 42 is rotated with the support shaft 41c as the rotation axis (rotation center) and is displaced from the state in FIG. 3 to the state in FIG. 4 (that is, when the optical filter 32 is moved from the first position to the second position), the through window portion 42bb of the filter retaining plate 42 and the through hole 41a of the main flat surface 41x of the base 41 become substantially coincident with each other, that is, the center of the through window portion 42bb and the optical axis O (optical path O4) become substantially coincident with each other.

Furthermore, the cam pin 42x, which is a protruding portion protruding from a surface facing the cam 43, in a direction parallel to the optical axis O (optical path O4), is provided to the filter retaining plate 42 in a protruding manner. The cam pin 42x is coupled with a cam groove 43c, described below, of the cam 43. Accordingly, when the cam 43 is rotated with the support shaft 41d as the rotation axis (rotation center) as described below, the cam pin 42x moves along the cam groove 43c, and the filter retaining plate 42 is thereby rotated with the support shaft 41c as the rotation axis (rotation center).

As described above, the cam 43, which is a transmission section, is installed near the drive motor 44, in a manner capable of rotating on a plane that is parallel to the main flat surface 41x with the support shaft 41d protruding in parallel to the optical axis O as the rotation axis (rotation center).

The cam 43 is formed from a disk portion 43a including a gear portion 43g at a partial region of an outer circumferential portion, and an arm portion 43b protruding from the disk portion 43a in a radially outward direction. The gear portion 43g of the disk portion 43a meshes with the drive gear 45 of the drive motor 44.

Moreover, the bottomed cam groove 43c for coupling with the cam pin 42x is formed to the arm portion 43b, on the side facing the filter retaining plate 42. The cam groove 43c is formed by including a first groove portion 43d, a second groove portion 43e, and a third groove portion 43f.

In other words, the cam 43 (transmission section) is a transmission section which includes the first groove portion 43d where the cam pin 42x (protruding portion) is to contact, and which moves the optical filter 32 (the filter retaining plate 42 retaining the optical filter 32) from the first position to the second position by rotating around the support shaft 41d (predetermined rotation shaft) and moving the cam pin 42x (protruding portion) along the first groove portion 43d. Moreover, the cam 43 (transmission section) is capable of moving the optical filter 32 (the filter retaining plate 42 retaining the optical filter 32) from the second position to the first position by moving the cam pin 42x (protruding portion) along the first groove portion 43d. That is, the first groove portion 43d is formed in a filter rotation region where the filter retaining plate 42 retaining the optical filter 32 may be rotated by the drive motor 44.

On the other hand, the second groove portion 43e of the cam 43 (transmission section) is provided along a tangent line direction of the cam pin 42x (protruding portion) centering around the support shaft 41d (rotation shaft) of the cam 43 (transmission section), in a state where the optical filter 32 (the filter retaining plate 42 retaining the optical filter 32) is moved to the second position. That is, the second groove portion 43e is formed inclined with respect to the first groove portion 43d. When the filter retaining plate 42 retaining the optical filter 32 is at the second position, that is, at a filter stop position, the second groove portion 43e serves to not transmit rotation torque to the drive motor 44 even if an overload is applied to the filter retaining plate 42 due to the self weight or the like.

On the other hand, the third groove portion 43f of the cam 43 (transmission section) is provided along the tangent line direction of the cam pin 42x (protruding portion) centering around the support shaft 41d (rotation shaft) of the cam 43 (transmission section), in a state where the optical filter 32 (the filter retaining plate 42 retaining the optical filter 32) is moved to the first position. That is, the third groove portion 43f is formed inclined with respect to the first groove portion 43d. When the filter retaining plate 42 retaining the optical filter 32 is at the first position, that is, at a filter stop position, the third groove portion 43f serves to not transmit rotation torque to the drive motor 44 even if an overload is applied to the filter retaining plate 42 due to the self weight or the like.

The drive motor 44, which is a drive source, is a general electric motor which is configured to be rotatable in forward and reverse directions. The drive motor 44 is fixedly installed on the main flat surface 41x of the base 41 by fixing means such as a screw, with the drive shaft 44a protruding in the orthogonal direction.

Moreover, the drive gear 45, which is a drive section, is a gear wheel which is rotated in forward and reverse directions by the drive motor 44. The drive gear 45 is fixed to the drive shaft 44a of the drive motor 44. Moreover, the drive gear 45 meshes with the gear portion 43g of the cam 43, as described above. With such a configuration, the cam 43 (transmission section) is rotated with the support shaft 41d as the rotation axis (rotation center) by the drive gear 45 which is rotated by the drive motor 44.

Note that, as described above, the gear portion 43g of the cam 43 is formed only at a partial region of the outer circumferential portion of the disk portion 43a. Accordingly, the cam 43 is rotatable only in a range where the gear portion 43g is formed. The same thing can be said for the filter retaining plate 42, which is rotated by the cam 43. That is, the filter retaining plate 42 (filter section) is provided on a plane perpendicular to the support shaft 41c as the rotation axis (rotation center), in a region within a predetermined angle around the support shaft 41c (rotation shaft).

The photointerrupter 46, which is a position detection section, is a structural component for detecting the position of the filter retaining plate 42 retaining the optical filter 32, that is, for detecting whether the filter retaining plate 42 is at the first position or the second position. The photointerrupter 46 is fixed to the base 41, and the filter retaining plate 42 is configured to move in a space between the photointerrupter 46 and the base 41. Note that the photointerrupter 46 is preferably arranged at a position away from the optical path O4 of illumination light. Moreover, the photointerrupter 46 may be configured to cover and block by using a cover member or the like (not shown) so as to suppress influence of illumination light.

An action of the drive device of the observation light switching mechanism unit 24 in the light source device 20, for an endoscope, of the control unit 19 of the endoscope system 1 according to the present embodiment configured in the above manner will be described below.

First, the drive device of the observation light switching mechanism unit 24 is assumed to be in the state shown in FIG. 3. As described above, the state shown in FIG. 3 is a state where the filter retaining plate 42 retaining the optical filter 32 is at the first position at which the filter retaining plate 42 is retracted from the optical axis O (optical path O4). In this state, the cam pin 42x engages with the third groove portion 43f of the cam groove 43c.

As described above, in the state where the optical filter 32 (filter retaining plate 42) is at the first position, the third groove portion 43f is along the tangent line direction of the cam pin 42x (protruding portion), which is on a circle having the support shaft 41d (rotation shaft) of the cam 43 (transmission section) at the center.

Accordingly, in such a state, for example, even if a force is unintentionally applied to the filter retaining plate 42 provided with the cam pin 42x, in a direction of rotating the filter retaining plate 42 around the support shaft 41d, the filter retaining plate 42 may be kept in an immobile state. Accordingly, unnecessary load is not transmitted to the drive motor 44.

Next, in this state, that is, with respect to the observation light switching mechanism unit 24 in the state where the optical filter 32 (filter retaining plate 42) is at the first position, supply of power to the drive motor 44 is started at an arbitrary timing, and the drive shaft 44a of the drive motor 44 is rotated along an arrow R1 shown in FIG. 3 (clockwise direction in FIG. 3). Then, the drive gear 45 is rotated in the same direction. Thus, the gear portion 43g of the cam 43, which meshes with the drive gear 45, is rotated along an arrow R2 shown in FIG. 3 (counterclockwise direction in FIG. 3).

In response, the cam 43 starts rotating in the direction of the arrow R2 in FIG. 3, with the support shaft 41d as the rotation axis. At this time, the cam pin 42x is removed from the third groove portion 43f, and enters the first groove portion 43d and moves along the first groove portion 43d. The filter retaining plate 42 is thereby rotated in the same direction as the arrow R2 in FIG. 3 (counterclockwise direction) with the support shaft 41c as the rotation axis. The state shown in FIG. 4 is then reached.

As described above, the state shown in FIG. 4 is a state where the filter retaining plate 42 retaining the optical filter 32 is at the second position at which the filter retaining plate 42 is inserted in the optical axis O (optical path O4). When such a state is reached, the cam pin 42x engages with the second groove portion 43e of the cam groove 43c.

When such a state is reached, for example, even if a force is unintentionally applied to the filter retaining plate 42 provided with the cam pin 42x, in a direction of rotating the filter retaining plate 42 around the support shaft 41d, the filter retaining plate 42 may be kept in an immobile state. Accordingly, unnecessary load is not transmitted to the drive motor 44.

As described above, according to the embodiment, because the filter retaining plate 42 (filter section) retaining the optical filter 32 for generating light of a predetermined wavelength characteristic can be arranged on a plane perpendicular to the support shaft 41c (rotation shaft), at the first position and the second position in a region within a predetermined angle around the support shaft 41c, the filter retaining plate 42 may be rotated with the support shaft 41d as the rotation center by providing the cam pin 42x (protruding portion) to the filter retaining plate 42 and moving the cam pin 42x along the first groove portion 43d of the cam 43 (transmission section). In such a case, in the state where the optical filter 32 is at the second position, the second groove portion 43e provided to the cam 43 is along the tangent line direction of the cam pin 42x, which is on a circle having the support shaft 41d of the cam 43 at the center. Also, in the state where the optical filter 32 is at the first position, the third groove portion 43f provided to the cam 43 is along the tangent line direction of the cam pin 42x on the circle having the support shaft 41d of the cam 43 at the center. Moreover, by providing the gear portion 43g, which meshes with the drive gear 45 which is rotated by the drive motor 44, to the cam 43, the cam 43 is rotated by the drive motor 44.

With such a configuration, when the filter retaining plate 42 is rotated and moved between the first position and the second position, the cam pin 42x is smoothly moved along the first groove portion 43d of the cam 43. On the other hand, in a state where the filter retaining plate 42 is at the first position or the second position, the cam pin 42x engages with the second groove portion 43e or the third groove portion 43f of the cam 43 such that transmission of rotation load of the filter retaining plate 42 to the drive shaft 44a of the drive motor 44 can be suppressed.

Moreover, overloading of the drive motor 44 may be suppressed simply by modifying the shape of the cam groove 43c provided to the cam 43. Accordingly, the device may be miniaturized, and at the same time, the manufacturing cost may be reduced.

Note that, in the embodiment described above, an example is described where the base, the filter retaining member and the like are formed by bending flat metal plate members, but such a configuration is not restrictive, and molded products of resin may also be used, for example.

Also, in the embodiment described above, the rotational force of the drive motor is transmitted to the cam by the drive gear, but such a configuration is not restrictive. For example, a mode in which the drive shaft of the drive motor is made coincident with the rotation axis (in the embodiment described above, the support shaft 41d) of the cam, that is, a mode in which the cam is pivotally and rotatably supported by the drive shaft of the drive motor and the cam is directly rotated by rotation of the drive motor is also possible.

In the embodiment described above, an example is described where one optical filter is provided to the filter retaining plate, but such a mode is not restrictive. For example, the filter retaining plate may be configured to retain a plurality of optical filters. In such a case, a cam groove which is along the tangent line direction of the cam pin (protruding portion) centering on the rotation axis of the cam may be provided at each predetermined position of a cam groove of the cam in a corresponding manner to the position of a corresponding optical filter when the corresponding optical filter is arranged at a predetermined position, that is, at a through hole of the main flat surface of the base, i.e., on the optical path (filter stop position).

Furthermore, the drive motor is a structural component which is a heat source, and is desirably provided outside a housing of the light source device for an endoscope. Also, in such a case, the drive motor is desirably provided near an air inlet, provided to a power supply unit, inside a housing of the control unit.

In the embodiment described above, the cam groove (groove portion) is provided on the side of the cam (transmission section), and the cam pin (protruding portion) is correspondingly provided on the side of the filter retaining plate (filter section), for example. The configuration of the present invention is not limited to such an example.

For example, the cam pin (protruding portion) may be provided on the side of the cam (transmission section), and the cam groove (groove portion) may be provided on the side of the filter retaining plate (filter section). In the case of such a configuration, the second groove portion and the third groove portion may be formed along the tangent line direction of the cam pin (protruding portion) centering on the rotation axis of the filter retaining plate (filter section).

Note that the present invention is not limited to the embodiment described above, and various modifications and applications may, of course, be made within the scope of the invention. Furthermore, the embodiment described above includes inventions of various stages, and various inventions may be extracted by appropriately combining a plurality of structural elements disclosed herein. For example, if the problem to be solved can be solved and the advantageous effects can be achieved even when some structural elements are removed from all the structural elements shown in the embodiment, a configuration from which the structural elements have been removed can be extracted as an invention. Moreover, structural elements of different embodiments may be combined as appropriate. The invention is not limited by any specific embodiment other than the appended claims.

The present invention may be applied not only to an endoscope control device in the medical field, but also to an endoscope control device in the industrial field.

What is claimed is:

1. A drive device comprising:
a drive motor;
a transmission having a first rotation shaft driven by a drive force of the drive motor;
an optical filter extending in a plane perpendicular to an optical axis of the optical filter, the optical filter being configured to rotate around a second rotation shaft different from the first rotation shaft, the second rotation shaft extending in a direction parallel to the optical axis;
wherein the transmission includes a first groove and a second groove formed continuously with the first groove;
the optical filter having a protrusion in engagement with the first groove and with the second groove such that rotation of the first rotation shaft moves the protrusion to move the filter from a first position in which the protrusion is in the first groove to a second position in which the protrusion is in the second groove, the second position being different from the first position; and
the first groove extending in a first direction and the second groove extending in a second direction offset from a first direction, the second direction being along a tangent line direction passing through the protrusion that is on a circle having the first rotation shaft at a center and a radius that is a distance between the first rotation shaft and the protrusion, in a state where the filter is moved to the second position.

2. The drive device according to claim 1, wherein the transmission is configured to move the filter from the second position to the first position by moving the protrusion along the first groove in coordination with rotation of the transmission, and the transmission further includes a third groove formed continuously with the first groove, the third groove being provided along a tangent line direction passing through the protrusion on the circle having the first rotation shaft at the center and the radius that is the distance between the first rotation shaft and the protrusion, in a state where the filter is moved to the first position.

3. The drive device according to claim 1, wherein the filter is provided on a plane perpendicular to the second rotation shaft, in a region within a predetermined angle with the second rotation shaft at the center.

4. The drive device according to claim 1, further comprising:

a gear that is rotated by the motor, wherein
the transmission is rotated by the gear.

5. An endoscope apparatus comprising:

an endoscope;
a controller; and
a light source for the endoscope, the light source comprising a drive device according to claim 1.

* * * * *